(12) United States Patent
Markwort et al.

(10) Patent No.: US 8,501,503 B2
(45) Date of Patent: Aug. 6, 2013

(54) METHODS OF INSPECTING AND MANUFACTURING SEMICONDUCTOR WAFERS

(75) Inventors: Lars Markwort, Haimhausen (DE); Pierre-Yves Guittet, Unterschleissheim (DE)

(73) Assignee: Nanda Technologies GmbH, Unterschleissheim (DE)

( * ) Notice: Subject to any disclaimer, the term of this patent is extended or adjusted under 35 U.S.C. 154(b) by 0 days.

(21) Appl. No.: 13/457,219

(22) Filed: Apr. 26, 2012

(65) Prior Publication Data

US 2012/0276664 A1 Nov. 1, 2012

Related U.S. Application Data

(60) Provisional application No. 61/480,279, filed on Apr. 28, 2011.

(51) Int. Cl.
*H01L 21/66* (2006.01)

(52) U.S. Cl.
USPC ...................................... 438/16; 257/E21.67

(58) Field of Classification Search
USPC ...................................... 438/16; 257/E21.67
See application file for complete search history.

(56) References Cited

U.S. PATENT DOCUMENTS

| 7,768,637 | B2 * | 8/2010 | Schupp et al. | 356/237.5 |
| 2009/0290168 | A1 | 11/2009 | Hamamatsu et al. | |
| 2009/0316143 | A1 * | 12/2009 | Yokota et al. | 356/237.5 |

FOREIGN PATENT DOCUMENTS

| WO | WO 2009/121628 A2 | 10/2009 |
| WO | WO 2011/020589 A1 | 2/2011 |

OTHER PUBLICATIONS

Invitation to Pay Additional Fees mailed on Jul. 6, 2012 for PCT Application No. PCT/EP2012/001858 filed on Apr. 30, 2012, 5 pages.
Dabertrand et al. (2008). "Industrial characterization of scatterometry for advanced APC of 65 nm CMOS logic gate patterning", *Proc. Of SPIE* vol. 6922:69220W-1-69220W-12.
Markwort et al. (Apr. 1, 2010). "Full wafer macro-CD imaging for excursion control of fast patterning processes," *Proc. Of SPIE* vol. 7638:763807-1-763807-9.

\* cited by examiner

*Primary Examiner* — Lex Malsawma
(74) *Attorney, Agent, or Firm* — Silicon Valley Patent Group LLP

(57) ABSTRACT

A method of manufacturing a plurality of semiconductor wafers comprising micro-inspecting at least one location within at least one micro-inspected pattern field and determining at least one parameter value representing a property of the wafer at the micro-inspected location, macro-inspecting a plurality of locations within the at least one micro-inspected pattern field and determining, for each macro-inspected location of the macro-inspected pattern field, at least one parameter value representing the property of the wafer at the macro-inspected location based on the light intensity recorded for the macro-inspected location and on the at least one parameter value representing the property of the wafer at the micro-inspected location of this pattern field.

32 Claims, 10 Drawing Sheets

METHODS OF INSPECTING AND MANUFACTURING SEMICONDUCTOR WAFERS

CROSS-REFERENCE TO RELATED APPLICATION(S)

This application claims priority under 35 USC 119 to U.S. Provisional Application No. 61/480,279, filed Apr. 28, 2011, and entitled "Methods of Inspecting and Manufacturing Semiconductor Wafers," which is incorporated herein by reference.

BACKGROUND

1. Field

The present disclosure relates to methods of inspecting manufacturing semiconductor wafers.

2. Brief Description of the Related Art

Miniaturized devices, such as semiconductor devices, are manufactured by applying a plurality of processing steps to a semiconductor wafer. The processing may include a film forming processing to provide a resist layer on the wafer, an exposure processing to expose portions of the resist, a post-exposure bake processing, a development processing, an etching processing to etch exposed or non-exposed portions of the resist, a deposition processing to deposit material at exposed or non-exposed portions of the resist, and other suitable processings. The processings are controlled using suitable processing parameters, such as temperatures, concentrations, exposure doses and other settings. In view of a high throughput of the manufacture it is necessary to control each of the processings based on corresponding parameters such that a desired result is achieved at each processing. Inspection of the semiconductor wafer can be performed after one or more of the applied processings. Based on an inspection result it is possible to adjust one or more of the processing parameters.

The inspection can be performed using suitable inspection tools to measure various properties of the semiconductor wafer and of microstructures formed thereon. Some inspection tools use particle beams or light beams directed to the wafer in order to generate images of the wafer which can be further analyzed to confirm that the processing is performed as desired or to determine defects in the processed wafer. Inspection tools are generally divided into micro-inspection tools and macro-inspection tools.

Micro-inspection tools aim to detect features of very small or even the smallest manufactured microstructures having dimensions of 0.5 µm and below. Micro-inspection tools typically use magnifying optics to detect radiation originating from the inspected location. An advantage of micro-inspection tools is that a geometry or other properties of a microstructure can be directly verified and that deficiencies in these microstructures can be directly shown. A disadvantage of micro-inspection tools is the long time needed for inspection if a substantial portion of the whole surface of the wafer is to be inspected. If only portions of the surface of the wafer are inspected due to time considerations, there is a risk that certain deficiencies are not detected.

Macro-inspection tools aim to achieve a high throughput at the cost of a lower sensitivity to defects and of a lower spatial resolution of the generated images. Macro-inspection tools do not necessarily use magnifying optics to detect radiation emanating from the inspected locations. Macro-inspection tools have an advantage in that large portions of the wafers or the complete wafers can be inspected within a short time, and they have a disadvantage in that the properties of very small manufactured microstructures can not be directly derived from images or other data recorded by the macro-inspection tool.

It is desirable to extend the applicability of macro-inspection tools and micro-inspection tools and to obtain more detailed inspection information from a semiconductor wafer at a high throughput.

It is further desirable to use information obtained using one or more inspection tools in a manufacturing process of semiconductor wafers.

SUMMARY

The present invention has been made taking the above problems into consideration.

The present disclosure provides methods of inspecting a semiconductor wafer which allow to obtain valuable information about microstructures formed on the semiconductor wafer.

The semiconductor wafer may typically comprise a plurality of dies, wherein each die is a small block of semiconducting material on which a given functional circuit is fabricated. After completion of the manufacture of the wafer, the wafer is cut into pieces, wherein each peace comprises one die.

Each die may include a plurality of different pattern fields in which microstructures are arranged according to different arrangement patterns. For example, microstructures can be arranged in a regular repetitive arrangement pattern, such that a repetition period can be identified for the arrangement in one or two directions. There can be different pattern fields having different arrangement patterns having different repetition periods. Moreover, other pattern fields may have arrangements of microstructures which are irregular or random. Since the wafer includes a plurality of dies, there are corresponding pattern fields having same arrangement patterns of microstructures distributed across the wafer.

Some embodiments of the present disclosure perform macro-inspecting of at least a portion of a semiconductor wafer by directing measuring light simultaneously to plural pattern fields within one die, to plural dies, or to the whole wafer, imaging the illuminated plural pattern fields, plural dies or whole wafer, respectively, onto an array of detector elements and recording light intensities detected by the detector elements. Herein, each location on the wafer is simultaneously imaged onto one or more adjacent detector elements, wherein the smallest microstructures formed on the wafer are too small and lateral extensions of the detector elements are too large in order to resolve the microstructures on the wafer from the detected light intensities. Still, information obtainable from the detected light intensities is valuable information allowing to determine certain parameter values representing a property of the microstructures formed on the wafer.

In exemplary embodiments herein, the macro-inspecting further includes high-pass filtering of the recorded light intensities. This may have an advantage in that variations in the recorded image which have a low spatial frequency and which are caused by, for example, variations in a layer thickness are removed from the recorded image such that the intensity variations in high-pass filtered image are mainly caused by the patterns of the microstructures.

According to further exemplary embodiments herein, the at least one parameter value representing the property of the wafer at the macro-inspected location is determined based on the high-pass filtered light intensity recorded for the macro-inspected location and on the at least one parameter value representing the property of the wafer at the micro-inspected location of this pattern field. In such embodiments, the at least one parameter value representing the property of the wafer may include parameters which are related to the patterns of the microstructures formed in a lithography step, such as a line width, a side wall angle, a height, a footing, an undercut, a corner rounding and a critical dimension (CD). Moreover, in such embodiments, the at least one parameter value representing the property of the wafer may not include parameters which are related to manufacturing steps applied to the whole wafer without generating patterns on the wafer, such as applying a coating, performing a post-exposure bake and developing a resist.

In certain embodiments, the at least one property of the microstructures comprises a line width, a side wall angle, a height, a footing, an undercut, a corner rounding and a critical dimension (CD), an overlay shift and a layer thickness of the microstructures arranged at the macro-inspected location. It can be possible to determine properties of features of microstructures even though the microstructures can not be directly resolved by the detector used in the macro-inspecting.

Some embodiments of the present disclosure use micro-inspecting of one or more locations on the wafer, wherein the micro-inspecting comprises directing measuring radiation to the location and detecting radiation emerging from the location. The micro-inspecting may have a spatial resolution better than a length scale of the smallest microstructures formed within the inspected location. For example, such micro-inspection can be performed using a scanning electron microscope.

Moreover, the micro-inspecting may have a spatial resolution which is below the length scale of the smallest manufactured microstructures such that it is not possible to directly resolve these microstructures by such micro-inspection. However, the micro-inspection may produce a sufficiently large amount of data such that it is possible to determine parameter values representing properties of the microstructures at the inspected location by applying numerical methods to the obtained measuring data. Such micro-inspection can be performed by, for example, a scatterometer in which measuring light is focused on the location and wherein a wavelength spectrum of the light emerging from the location is recorded. The shape of the recorded spectrum is indicative of parameter values representing properties of the microstructures on the wafer. These parameter values can be determined by numerical analysis of the recorded spectra.

Some embodiments of the present disclosure use a combination of micro-inspecting and macro-inspecting of the wafer. Herein, the micro-inspecting is applied to a relatively low number of locations on the wafer and used to derive one or more parameter values representing properties of the wafer at the micro-inspected locations. The macro-inspecting is applied to a high number of locations in order to detect at least one light intensity for each of the macro-inspected locations. These detected light intensities alone would not be sufficient to directly obtain parameter values representing properties of the microstructures formed at the macro-inspected locations. However, by using the parameter values of the properties of the microstructures obtained by the relatively low number of micro-inspections, it is possible to relate the light intensities recorded for the relatively high number of macro-inspected locations to parameter values representing the properties of the microstructures at the respective macro-inspected locations.

In exemplary embodiments, the radiation of the micro-inspecting is focused to locations on the wafer having a diameter which is 2 times, 5 times, 10 times or even more than 50 times smaller than a diameter of a location imaged onto one detector element of the detector used in the macro-inspecting.

In further exemplary embodiments, the micro-inspecting uses highly magnifying optics to detect radiation emanating from the micro-inspected location. A magnification of the magnifying optics can be, for example, greater than 5 times, greater than 20 time or even greater than 100 times. In exemplary embodiments herein the macro-inspecting uses optics of a low magnification to detect radiation emanating from the macro-inspected locations. A magnification of these optics can be, for example, less than 2, less than 1, less than 0.7 or less than 0.4.

In certain embodiments, a number of macro-inspected locations on one wafer is much higher than a number of micro-inspected locations on the same wafer. For example, the number of macro-inspected locations can be greater than times, 100 times or even greater than 1000 times the number of micro-inspected locations.

In certain embodiments, the macro-inspecting uses light of a broad spectral range for the imaging. The spectral range may comprise visible light, infrared light and ultraviolet light.

In other embodiments, the macro-inspecting uses light of a narrow spectral range for the imaging. The narrow spectral range may be within visible light, infrared light or ultraviolet light.

In some embodiments, the macro-inspecting uses an imaging such that an area of the semiconductor wafer which is imaged onto one detector element of an array of detector elements has an extension of more than five times, more than ten times or more than fifty times of a smallest repetition period at which microstructures are arranged in a region. This means that it is not possible to observe or detect a geometry or structure of the microstructures formed in those regions using the detector with the array of pixels. In other words, the microstructures are too small to be directly observed using the imaging. However, a selected field in which the microstructures are arranged according to a same regular repetitive arrangement pattern is imaged onto a well-defined group of plural pixels of the detector.

In some embodiments, the disclosure provides for imaging of a selected pattern field onto a group of more than 5 detector elements, more than 10 detector elements, more than 25 detector elements or more than 35 detector elements. For example, a selected region can be imaged onto a group of 3×3 detector elements, 4×4 detector elements, 5×5 detector elements, 3×7 detector elements, 5×6 detector elements and so on. Moreover, the groups of detector elements do not need to occupy rectangular portions of the detector; the groups of detector elements can have arbitrary shapes substantially corresponding to the shapes of the selected pattern fields on the wafer.

In some embodiments, the disclosure provides for collecting detection signals from detector elements of a detector and calculating values from selected subsets of detection signals. Among the detection signals available from all detector elements of the detector, only selected subsets of detection signals are used for calculation of the values, and other detection signals are not used for or excluded from the calculation of those values. In other words, some detector elements are "masked" in that sense that detected intensities from those detector elements do not influence a result of the calculation of the plural values. The detection signals which do not influence the calculation result include detection signals from detector elements which are not members of any of those selected groups of detector elements onto which locations within selected pattern fields of the wafer are imaged, wherein the selected pattern fields are those regions in which microstructures are arranged according to a regular repetitive arrangement pattern. Detection signals which influence the calculation result comprise detection signals from the selected groups of detector elements onto which locations within the selected pattern fields are imaged.

In some embodiments, the macro-inspecting comprises determining a parameter value representing a property of the microstructures formed at at least one location of the wafer, which location is imaged onto one or more detector elements. In certain embodiments, the at least one property of the microstructures comprises a line width, a side wall angle, a height, a footing, an undercut, a corner rounding and a critical dimension (CD), an overlay shift and a layer thickness of the microstructures arranged at the macro-inspected location. It can be possible to determine properties of features of microstructures even though the microstructures can not be directly resolved by the detector used in the macro-inspecting.

In some embodiments, one or more locations within a given pattern field are macro-inspected to record one or more light intensities corresponding to the one or more macro-inspected locations. Also, at least one location within the same pattern field, or within a different pattern field having a same arrangement pattern of microstructures as the pattern field in which the macro-inspected locations are located, is micro-inspected in order to determine at least one parameter value representing a property of the microstructures at the micro-inspected locations. The at least one parameter value obtained from the micro-inspection is used to determine parameter values representing properties of the microstructures at the macro-inspected locations. Using such combination of micro-inspection and macro-inspection may allow to obtain highly significant parameter values representing properties of the microstructures at many macro-inspected locations using only a low number of micro-inspections. Since the macro-inspection of a high number of locations can be simultaneously performed within a short period of time and since only a relatively low number of micro-inspections can be sufficient, the combined macro-inspection and micro-inspection can produce a large amount of valuable information with respect to microstructures of the wafer at a high throughput.

According to exemplary embodiments, a method of manufacturing a plurality of semiconductor wafers comprises micro-inspecting at least one location within at least one micro-inspected pattern field and determining at least one parameter value representing a property of the wafer at the micro-inspected location, wherein the micro-inspecting comprises directing measuring radiation to the location and detecting radiation emerging from the location, and wherein a region on the wafer to which the measuring radiation is directed may have a first surface area, macro-inspecting a plurality of locations within the at least one micro-inspected pattern field, wherein the macro-inspecting comprises directing measuring light, in particular simultaneously, to plural pattern fields, plural dies or the whole wafer, imaging the illuminated plural pattern fields, dies and whole wafer, respectively, onto an array of detector elements and recording light intensities detected by the detector elements, wherein each of the locations is simultaneously imaged onto one or more adjacent detector elements. The macro-inspected location may have a second surface area which is at least 2 times greater, or at least 5 times or 10 times greater, than the first diameter. Further, a number of the macro-inspected locations within each of the at least one micro-inspected pattern fields may be at least 5 times greater than a number of the micro-inspected locations within this pattern field. The method may further comprise determining, for each macro-inspected location of the macro-inspected pattern field, at least one parameter value representing the property of the wafer at the macro-inspected location based on the light intensity recorded for the macro-inspected location and on the at least one parameter value representing the property of the wafer at the micro-inspected location of this pattern field.

According to some embodiments herein, the method further comprises processing the wafers using at least one processing parameter and changing the at least one processing parameter based on the parameter values determined for the macro-inspected locations.

According to further exemplary embodiments, a method of manufacturing a plurality of semiconductor wafers comprises processing the wafers using at least one process parameter, and changing the at least one process parameter based on the parameter values determined for the macro-inspected locations.

According to some embodiments herein, the at least one statistical property comprises a moment of a distribution of the values for each wafer. According to exemplary embodiments herein, the at least one statistical property comprises a mean value, a variance, a skewness or a kurtosis.

According to some embodiments, the macro-inspecting comprises providing at least two different light settings and recording light intensities detected by the detector elements for each of the at least two different light settings. A group of light intensities are detected at each individual light setting. A subset of light intensities is selected from each group of light settings according to whether or not the respective light intensities are recorded by detector elements onto which a portion of the selected pattern fields is imaged. Light intensities from the plural resulting subsets are used to determine plural values forming the bases for determining the at least one statistical property. Herein, each value is determined from those light intensities in the plural subsets which are recorded by same detector elements. For example, two light settings may differ with respect to polarization of the light recorded by the detector elements. Each value forming the bases for determining the statistical property can be determined from the light intensity recorded by a given detector element at the first polarization setting and the light intensity recorded by the same detector element at the second polarization setting. For example, the determined value can be calculated by dividing the recorded light intensity of the detector element recorded at the first polarization setting by the light intensity recorded by the detector element at the second polarization setting.

According to some embodiments, the changing of the at least one processing parameter is based on a comparison of the determined statistical property with a predetermined value of the statistical property and without using any information obtained by micro-inspecting of the wafer. It is then possible to assess a quality of the manufactured semiconductor wafers by macro-inspecting and without performing any micro-inspection.

The inventors have found that the statistical analysis of light intensities obtained from macro-inspection is highly indicative of changes in the manufacturing process of plural wafers. Therefore, if the statistical property, such as a mean, a variance, a skewness or a kurtosis of the recorded light intensity changes, such changes are indicative of changes of processing parameters involved in the semiconductor wafer manufacture. According to some embodiments, the change of the statistical property of the values triggers a signal requesting an operator to check and update the processing parameters of the manufacture, or an automatic system for manufacturing the wafers can be triggered in order to update the processing parameters.

In some embodiments the processing comprises a deposition, such as a chemical vapor deposition (CVD) and a physical vapor deposition (PVD), wherein the at least one processing parameter comprises a concentration, a temperature and a duration.

In certain embodiments, the disclosure provides a processing comprising exposing of a substrate with a pattern, wherein the at least one processing parameter comprises an exposure dose and/or a focus used in the exposing.

In some embodiments, a processing of a substrate comprises etching of the substrate, wherein at least one processing parameter comprises an etch time, an etch temperature and a concentration of a medium used in the etching.

According to embodiments, a method of manufacturing semiconductor wafers comprises coating the wafer with a resist; exposing a pattern onto the resist after the coating; developing the patterned resist after the exposing; etching the wafer through the developed resist after the developing; and removing the resist remaining on the wafer after the etching; wherein a combined macro-inspecting and micro-inspecting or only a macro-inspecting of the wafer is performed after the etching of the wafer and before the removing of the remaining resist. The removing of the remaining resist may comprise a processing, such as ashing to burn off a remaining resist polymer, and a subsequent step of cleaning to remove residue and resist particles.

According to some embodiments, a method of manufacture of a semiconductor wafer includes macro-inspecting the semiconductor wafer, wherein the macro-inspecting comprises: positioning the wafer relative to an imaging optics and a camera having an array of detector elements such that the wafer is imaged onto the camera by the imaging optics; directing illuminating light produced by a light source onto the wafer; providing a first light setting and recording a first image of the wafer with the camera using illuminating light reflected from the wafer; and providing a second light setting and recording a second image of the wafer with the camera using illuminating light reflected from the wafer; wherein the first and second light settings differ with respect to at least one of a polarization and a spectrum of the light used for imaging the wafer onto the detector.

According to some embodiments, the first and second light settings are produced by at least one optical filter provided in at least one of a beam path between the light source and the wafer and a beam path between the wafer and the camera, wherein the optical filter can be changed such that a polarization of the light traversing the filter changes and/or such that a spectral distribution of intensities of the light traversing the filter changes.

According to some embodiments, the first and second light settings are produced by changing a light source generating the illumination light. For example plural light sources, such as plural LEDs, providing different spectral ranges of illumination light can be provided and selectively operated to selectively generate illumination light of different spectral distributions.

According to exemplary embodiments herein, even more than two images can be recorded at more than two light settings.

According to exemplary embodiments, a position of the wafer relative to the imaging optics and camera is maintained constant between the recording of the first image and the recording of the second image, such that an image processing applied to the plural recorded images is facilitated and that results of image processing can be readily associated with particular locations and pattern fields of the wafer.

According to some embodiments, the light with which the first image is recorded has a first spectral distribution and the light with which the second image is recorded has a second spectral distribution, and wherein the first and second light settings are configured such that a central wavelength of the first spectral distribution differs from a central wavelength of the second spectral distribution by more than 30 nm, more than 50 nm or more than 100 nm. The central wavelength can be calculated according to one of the methods known in the art. For example, the central wavelength can be calculated by determining a center of gravity of an area below a graph representing the spectral distribution of the light used.

According to some embodiments, a width of each of the first and second spectral distributions is smaller than 100 nm or smaller than 50 nm. The width of the spectral distribution can be calculated according to one of the methods known in the art. For example, the width of the spectral distribution can be calculated by determining upper and lower bounds of a portion of the spectral distribution such that, for example, 90% of the spectral intensity are contained within a wavelength range defined by the upper and lower bounds. The difference between the upper bound and the lower bound will then represent the width of the spectral distribution.

According to other embodiments, the light with which the first image is recorded has a first polarization direction and the light with which the second image is recorded has a second polarization direction, and wherein the first and second light settings are configured such that the first polarization direction differs from the second polarization direction by more than 10°, by more that 20° or by more than 40°. Herein, it is possible that the light is only partially polarized since a perfect linear polarization of 100% is difficult to obtain in practice. Moreover, according to further embodiments, the first polarization differs from the second polarization with respect to a degree of polarization. For example, the first image can be recorded using non-polarized light while the second image is recorded using light having a degree of polarization of, for example 60%.

According to some embodiments, the light setting is changed by changing a filter provided in an illumination beam path of an inspection system. According to other embodiments, the light setting is changed by changing a filter provided in an imaging beam path of an inspection system, and according to still further embodiments, the filter setting is changed by changing both a filter provided in an illumination beam path of an inspection system and a filter provided in an imaging beam path of the inspection system. The changing of the filter may include replacing a first filter having a first transmission characteristics positioned in the beam path with a second filter having a second transmission characteristics. The transmission characteristics may differ with respect to a spectral distribution of intensities and/or with respect to a polarization of the light transmitted trough or reflected from the filter.

According to some other embodiments, the light setting is changed by changing a light source generating the illumination light in an illumination beam path of an inspection system.

In some embodiments, the macro-inspecting involves imaging at least a portion of a substrate onto a detector. According to some embodiments herein, the complete surface of the substrate is imaged onto the detector.

BRIEF DESCRIPTION OF THE DRAWINGS

The foregoing as well as other advantageous features of the disclosure will be more apparent from the following detailed description of exemplary embodiments, the drawings and the claims.

DETAILED DESCRIPTION

Figure 2:
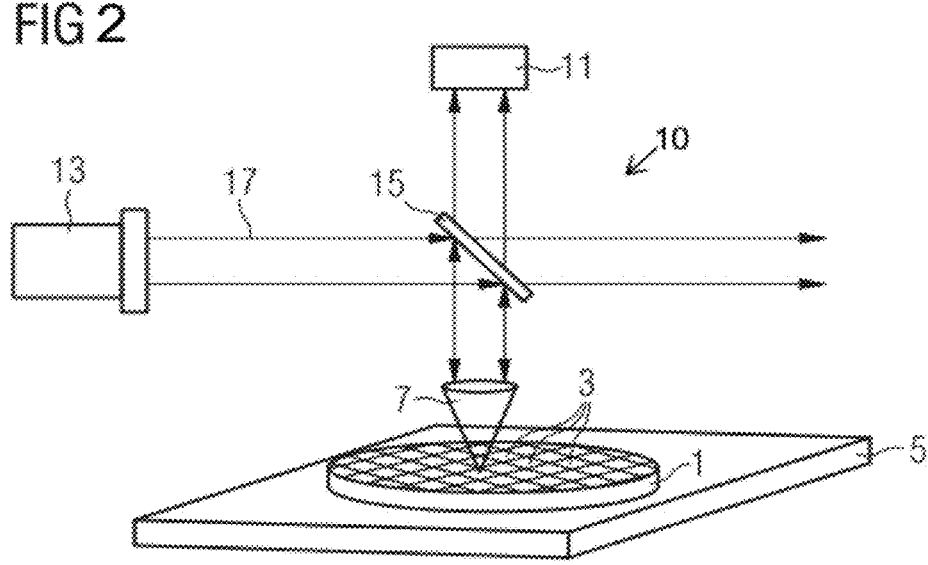
FIG. 2 is a schematic illustration of micro-inspection system.

In the exemplary embodiments described below, components that are alike in function or in structure are generally designated by like reference numerals.

Figure 1:
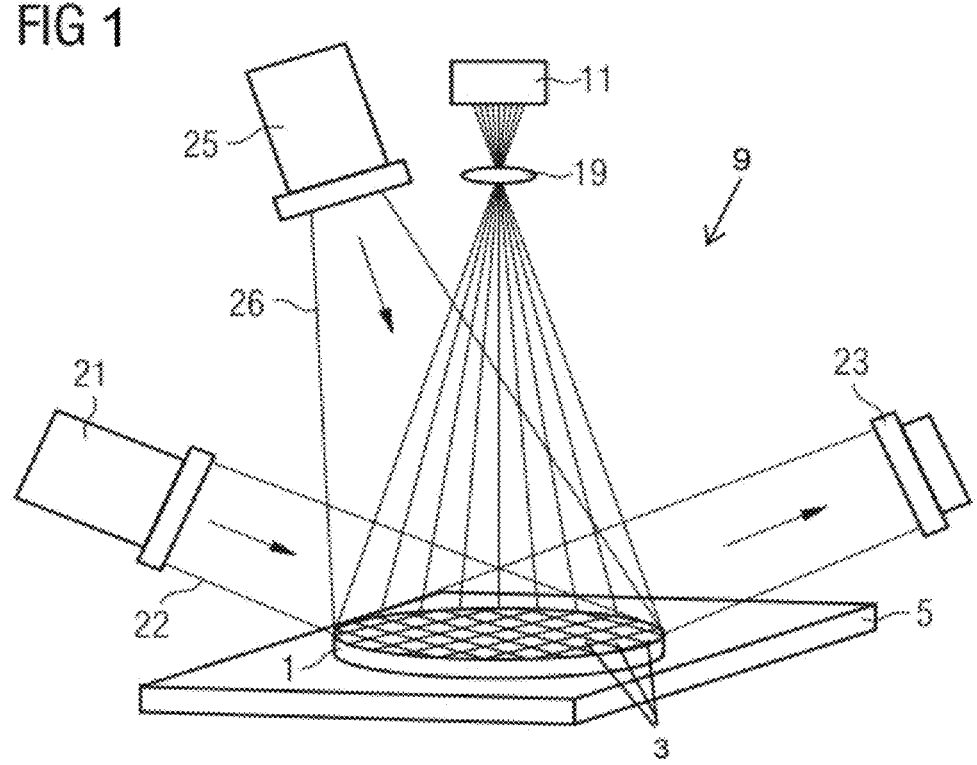
FIG. 1 is a schematic illustration of a macro-inspection system.

FIG. 1 illustrates a macro-inspection system which can be used in methods of manufacturing semiconductor wafers. The macro-inspection system 9 is used to image a larger portion including plural dies 3 on a surface of a wafer 1, or the whole wafer surface, onto an image detector 11 having an array of detector elements while the wafer is mounted on a wafer stage 5. Since a size of available image detectors can be smaller than a size of the portion of the wafer imaged onto the detector, de-magnifying imaging optics 19 can be used to image the portion of the wafer onto the detector 11. The macro-inspection system further comprises a dark field light source 21 for generating a dark field illumination beam 22 directed under an acute angle onto the wafer surface such that a main portion of the incident dark field illumination light beam is specularly reflected from the wafer surface and trapped in a beam dump 23. Certain structures on the wafer scatter the incident dark field illumination light such that it is collected by the imaging optics 19 and such that scattering structures are imaged onto the detector 11. The macro-inspection system 9 further comprises a bright field light source 25 for generating a bright field illumination light beam 26 incident onto the wafer surface such that a significant portion of the bright field illumination light is reflected from the wafer and collected by the imaging optics such that structures on the wafer can be imaged onto the image detector 11 using the bright field illumination light.

The macro-inspection system has an advantage in that a huge number of locations on the wafer corresponding to a number of detector elements of the detector can be simultaneously imaged onto the detector within a short period of time. A disadvantage of the macro-inspection system lies in the fact that microstructures provided on the wafer have characteristic dimensions which are substantially smaller than the lateral extension of a location on the wafer which is imaged onto one detector element such that the microstructures can not be directly resolved in such imaging due to the limited resolution of the array of detector elements.

While the illustration of the macro-inspection system shown in FIG. 1 is very schematic in order to illustrate the principles of macro-inspection, more detailed information relating to macro-inspection systems which can be used in embodiments according to the present disclosure are illustrated in WO 2009/121628 A2 and WO 2011/020589 A1, wherein the contents of these documents are incorporated herein by reference in their entirety.

FIG. 2 is a schematic illustration of an optical micro-inspection system which can be used in methods of manufacturing semiconductor wafers. The micro-inspection system 10 shown in FIG. 2 has a configuration of a microscope and comprises an image detector 11, a light source 13 and a beam splitter 15. A portion of a measuring light beam 17 generated by the light source 13 is reflected from the beam splitter 15, traverses an objective lens 7 and is focused by the objective lens to illuminate a location on the wafer 1. The illuminated location of the wafer is imaged onto the image sensor such that a magnified microscopic image of the location of the wafer can be detected. The wafer 1 is mounted on a wafer stage 5 which is configured to translate and rotate the wafer relative to the objective lens 7 such that plural locations on the wafer can be subsequently inspected. While the micro-inspection system 10 shown in FIG. 2 has the configuration of an imaging microscope, other configurations of optical micro-inspection systems are possible. For example, a micro-inspection system may comprise a spectrometer disposed in a beam paths between the objective lens and the detector. The spectrometer produces a dispersion such that reflected light intensities can be recorded in dependence of the wavelength of the reflected light. As an alternative, or in addition thereto, one or more polarizers can be located in the beam path between the light source, the wafer and the detector in order to detect light intensities depending on polarization. An analysis of recorded spectra of measuring light originating from the inspected location allows to determine parameter values representing certain properties of microstructures formed on the wafer. Such analysis may involve modeling of the microstructures using a software system and solving Maxwell's equations for such modeled structures. This type of analysis is also referred to as "rigorous analysis". An example of a micro-inspection system which can be used in embodiments of methods of semiconductor wafer manufacture according to the present disclosure are systems available from Nanometrics, Inc., Milpitas, Calif., under the names "Atlas XP" and "IMPULSE".

Figure 3:
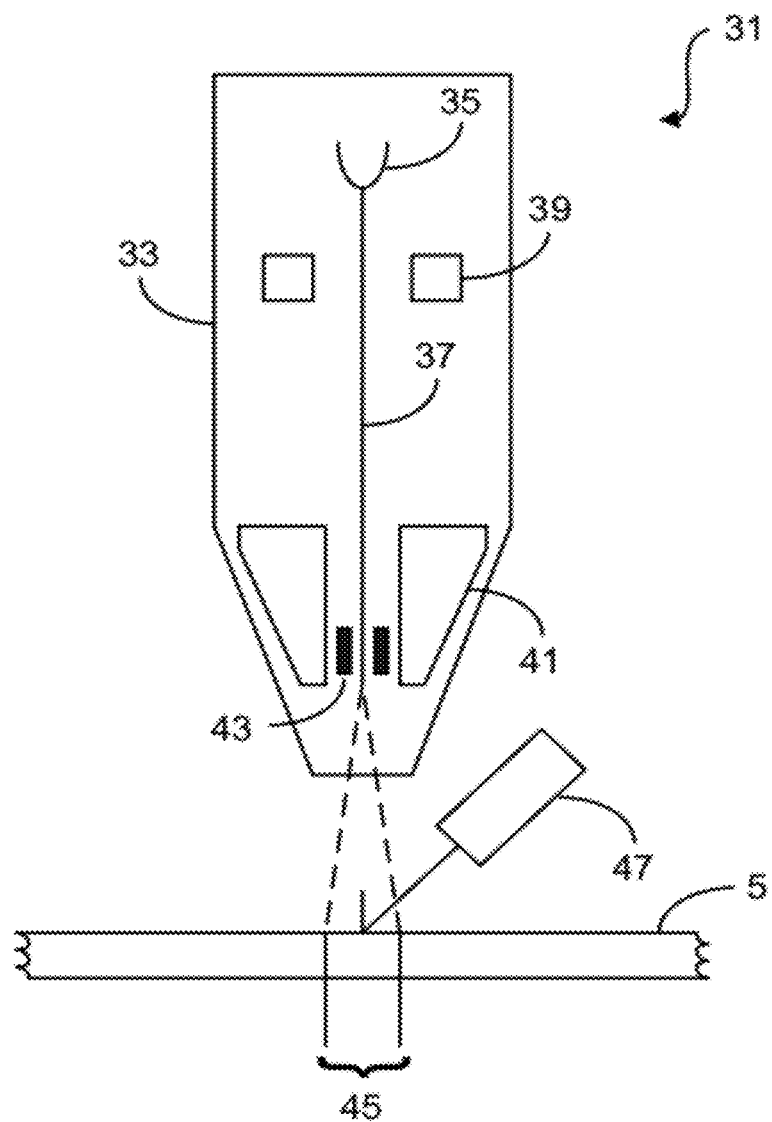
FIG. 3 is a schematic illustration of a further micro-inspection system.

FIG. 3 is a schematic illustration of a further micro-inspection system which can be used in methods of manufacturing semiconductor wafers. The system illustrated in FIG. 3 is a scanning electron microscope 31 comprising a beam column 33 having an electron beam source 35 for generating an electron beam 37. The electron beam 37 is collimated by a condenser lens 39 and focused onto a surface of a wafer 1 by an objective lens 41. The beam column 33 also includes deflectors 43 for scanning the electron beam across an inspected location 45 on the wafer surface. A secondary electron detector 47 is provided to detect secondary electrons emerging from the wafer 1 due to the incidence of the electron beam 37. The scanning electron microscope 31 can be used for generating an electron optical image of the location 45 such that microstructures provided on the wafer are directly visible in this image. Parameter values representing properties of the microstructures, such as a critical dimension, can be derived from the image. The micro-inspection using the scanning electron microscope 31 can be repeated, one after the other, by displacing the a wafer stage (not shown in FIG. 3) on which the wafer is mounted relative to the microscope.

The micro-inspection systems shown in FIGS. 2 and 3 have an advantage that parameter values representing properties of the microstructures formed on the wafer can be measured with a high accuracy. However, these systems have the disadvantage of low throughput.

Figure 4:
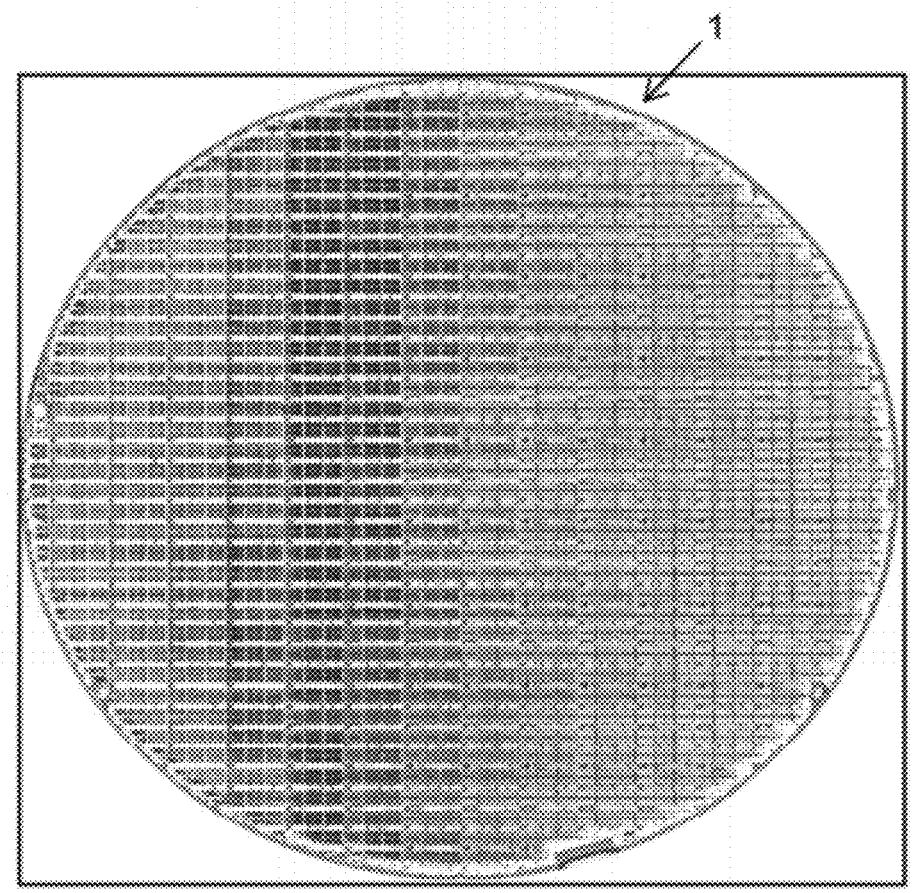
FIG. 4 is a representation of an image of a semiconductor wafer recorded with a macro-inspection system.

FIG. 4 shows an image of a patterned semiconductor wafer recorded with a macro-inspection system which can be used in methods of manufacturing semiconductor wafers. The wafer 1 has a diameter of about 300 mm, and the image represents detection signals recorded by detector elements of the detector 11, wherein dark portions of the image represent low detected light intensities and the bright portions of the image represent high detected light intensities. The detector elements or pixels of the detector are arranged in a two-dimensional 3000×3000 array totaling in 9 million detector elements. With such an arrangement, an area of about 100 µm×100 µm on the wafer is imaged onto one detector element of the detector or, in other words, each pixel of the image represents an intensity of light collected from an area of about 100 µm×100 µm of the wafer 1.

The patterns visible in the image of the wafer correspond to plural identical exposure fields, each generated in subsequent exposure steps.

Figure 5:
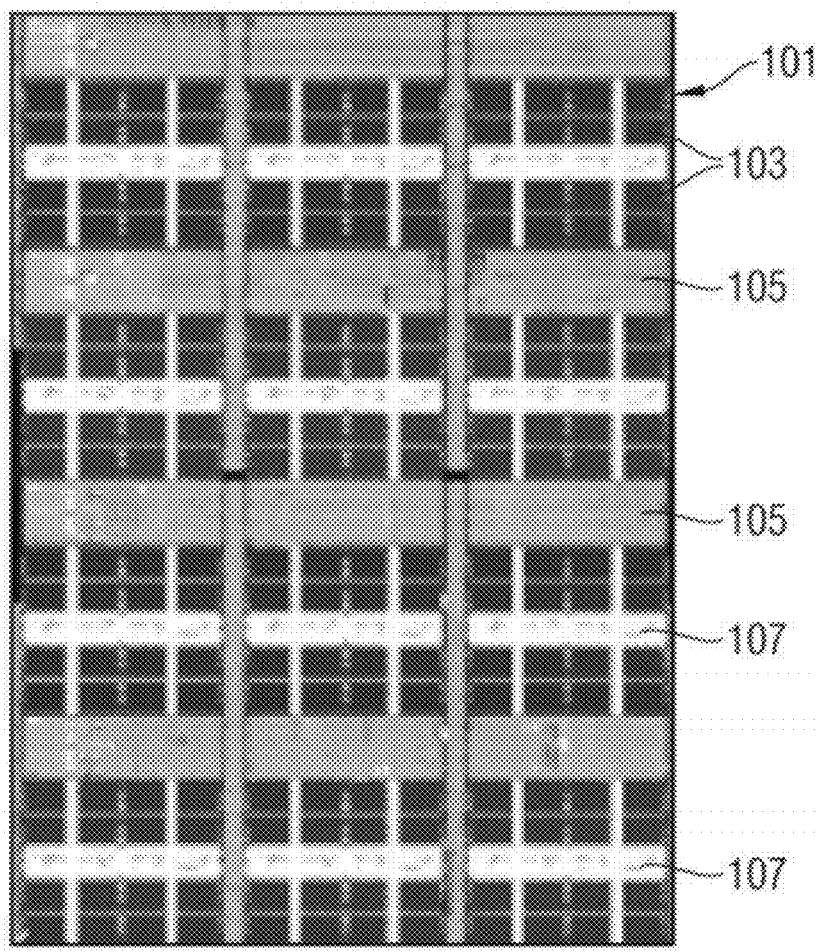
FIG. 5 is an image of an exposure field of the wafer shown in FIG. 4.

FIG. 5 is an enlarged view of one such exposure field 101 which has, in the illustrated example, a horizontal extension of 26 mm and a vertical extension of 33 mm. In the illustrated example, the exposure field 101 corresponds to plural dies which will, upon completion of the manufacture of the wafer, form plural functional semiconductor circuits or chips. It is apparent from figure that each die has different types of regions, such as black regions, grey regions and white regions arranged in a manhattan pattern. The different regions correspond to different arrangement patterns of microstructures formed on the wafer substrate. The black regions 103 of the image correspond to fields on the wafer where a semiconductor memory is formed, the grey regions 105 of the image correspond to fields on the wafer where main logic support structures are formed, and the white regions 107 of the image correspond to fields on the wafer where logic sub-structures are formed. The semiconductor memory pattern fields 103 are formed by microstructures arranged in a highly regular repetitive arrangement pattern with a smallest repetition period of about 70 nm in the horizontal and vertical directions in this illustrated example.

Figure 6:
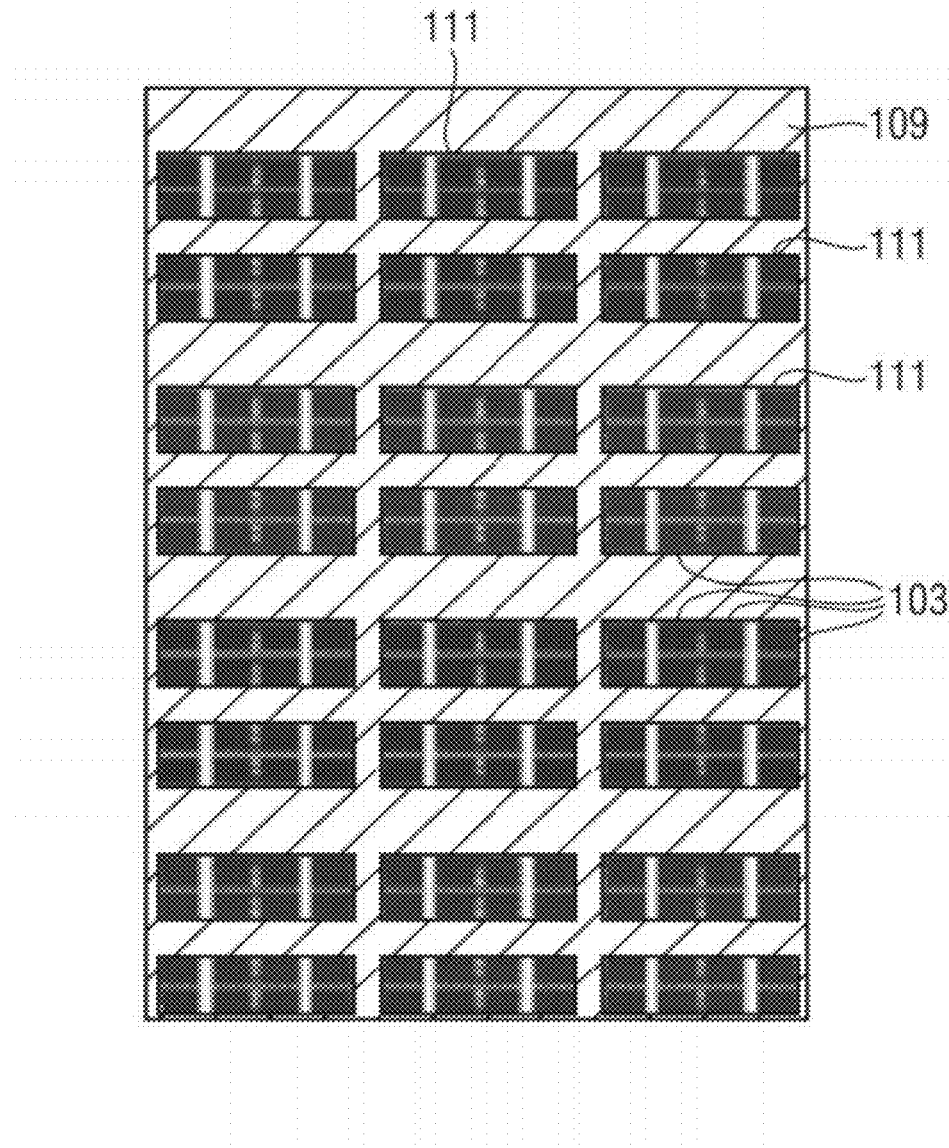
FIG. 6 is a schematic illustration of a mask which can be overlayed on the image shown in FIG. 5.

The memory pattern fields 103 are selected for further analysis by applying a mask 109 shown in FIG. 6 as hatched portions. The mask 109 covers the horizontal and vertical portions of the grey pattern fields 105 and the horizontal portions of the white pattern fields 107 shown in FIG. 5. The portions of the image 101 coinciding with the mask 109 are excluded from the further analysis. The further analysis is directed to a subset of light intensities recorded by detector elements corresponding to pixels of the image 101 coinciding with windows or openings 111 of the mask 109. Those pixels of the image corresponding to one opening 111 of the mask are each grouped into a selected group of pixels, wherein one or more measurement values are calculated from each selected group of pixels. In the illustrated example, one single value is calculated by averaging the image intensities of the pixels of each group. Since the mask 109 shown in FIG. 7 has 3×8 openings 111, 24 values are calculated for each exposure field 101 of the wafer 1.

The following table 1 shows an example of such values obtained for an exemplary masked exposure field as shown in FIG. 6.

TABLE 1

| 1860 | 1828 | 1845 |
|------|------|------|
| 1884 | 1852 | 1869 |
| 2164 | 2123 | 2134 |
| 2105 | 2080 | 2110 |
| 2013 | 2012 | 1988 |
| 1887 | 1847 | 1880 |
| 1846 | 1817 | 1820 |
| 1835 | 1819 | 1828 |

It is apparent that the averaged intensity values are not identical for all of the selected regions of the wafer corresponding to the respective windows 111, even though the microstructures formed in the respective memory pattern fields are expected to be the same. It is to be noted that it is not possible to directly image the microstructures with the inspection system of FIG. 1 using the detector with 9 million pixels since the microstructures are much smaller than the area of 100 µm×100 µm imaged onto one pixel of the detector.

It has been found that the averaged intensity values shown in the table above are indicative of variations of feature properties of the microstructures in the different selected pattern fields 111. Those feature properties are not perfectly identical for all regions 111 of the exposure field. In fact, the feature properties are slightly varied from pattern field to pattern field. It has been found that already slight variations of the feature properties result in noticeable differences of the averaged values as shown in Table 1 above.

In the illustrated example, the variations of the averaged values are attributed to variations of a critical dimension with which the microstructures are formed on the wafer. In other examples, the variations of feature properties which correspond to variations of the averaged values may comprise a line width, a side wall angle, a height, a footing, an undercut and a corner rounding of features of microstructures, an overlay shift between structures of a current or top layer relative to structures of a preceding layer covered by the top layer, and layer thicknesses of the features of the microstructures or other feature properties.

According to some example, the image recorded in the macro-inspection, such as the image shown in FIG. 4, is processed by applying a high-pass filter to the image. Such high-pass filter will remove variations in the recorded image which have a low spatial frequency and which are caused by, for example, variations in a layer thickness. Intensity variations in high-pass filtered image are mainly caused by the patterns of the microstructures which are formed in lithography steps. In such example, the at least one parameter value representing the property of the wafer may include parameters which are related to the patterns of the microstructures formed in a lithography step, accordingly, such as a line width, a side wall angle, a height, a footing, an undercut, a corner rounding and a critical dimension (CD). Moreover, in such examples, the at least one parameter value representing the property of the wafer will not include parameters which are related to manufacturing steps applied to the whole wafer without generating patterns on the wafer, such as applying a coating, performing a post-exposure bake and developing a resist. The high-pass filtering of the image recorded in the macro-inspection is applied to the image before the parameter value representing the property of the wafer is determined. The high-pass filtered image is then used for determining the at least one parameter value representing the property of the wafer. Such high-pass filtering of the recorded image can be used in all embodiments illustrated in more detail below. Moreover, a similar result can be achieved in all those embodiments, if a low-pass filtered image is produced from the image recorded in the macro-inspection, and wherein the low-pass filtered image is subtracted from the recorded image.

In the illustrated example, one value is calculated by averaging of the detection signals collected from one group of pixels. In other examples, one value or plural values can be calculated by other mathematical operations from the selected group of detection signals. The mathematical methods may comprise a statistical analysis, a determination analysis, a calculation of an average, a calculation of a median, a calculation, of a variance, a calculation of a standard deviation. These one or more calculated values can be again indicative of variations of feature properties of the microstructures formed on the substrate. The number of values calculated from a selected group of pixels can be less than the number of pixels in the group. For example, the number of pixels in the group can be greater than 5 or greater than 10, while the number of values calculated from the group can be less than 5 or equal to 1. According to another example, the number of pixels in the group is greater than 40, while the number of values calculated from the group can be less than 10 or, in particular, equal to 1.

According to still further examples there is one pixel in a group, such that the value is calculated from one single pixel and encodes the light intensity detected by one pixel or a function of this light intensity. In such example, the number of values is equal to the number of pixels in the group.

In the example illustrated with reference to FIG. 7, the mask covers the horizontal and vertical portions of the grey pattern fields 105 and the horizontal portions of the bright pattern fields 107, while the narrow vertical portions of the white pattern fields are not completely covered by the mask. The mask can be further improved by also covering the narrow vertical portions of the white pattern fields 107, such that each group of pixels corresponding to a window in the mask would correspond to exactly one memory portion of the wafer. In other examples, other shapes of the mask can be found which would also allow to obtain values which are indicative for feature properties of microstructures formed in selected pattern fields of the wafer.

Figure 7:
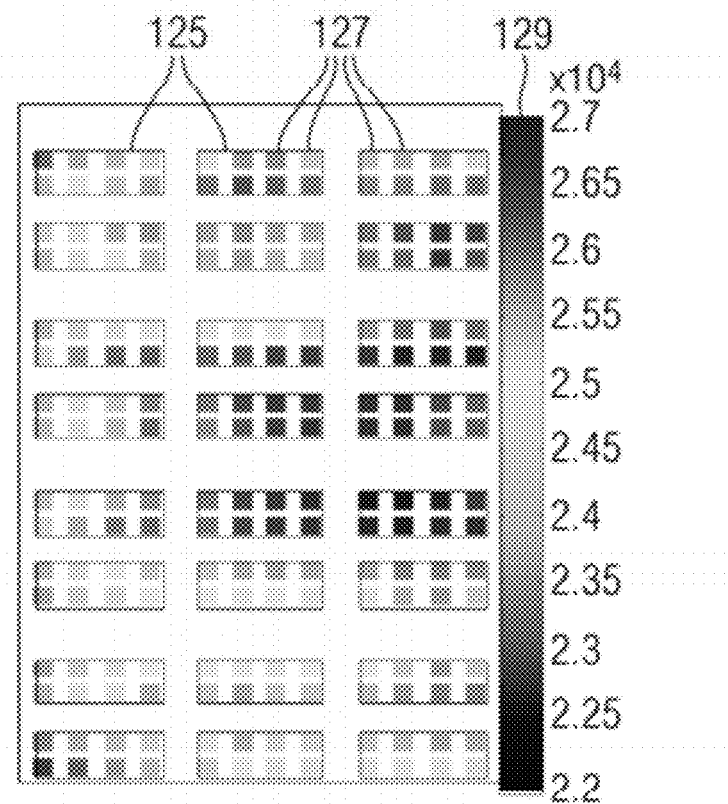
FIG. 7 is a schematic illustration of an intermediate result of a calculation.

FIG. 7 shows a result of a processing using a mask, wherein each window in the mask corresponds to exactly one memory portion of the wafer 1. Rectangles 125 in FIG. 7 correspond to the windows 111 of the mask 109 shown in FIG. 6. In this illustrated example, however, the mask comprises windows represented by shaded rectangles 127 in FIG. 7. Each window of this mask corresponds to one memory portion 103 of the wafer 1. For each such window of the mask, a processing with groups of pixels is performed as illustrated above, wherein one result value is calculated from each group of pixels. The result value is represented in FIG. 7 as a grey value of the shaded rectangles, wherein a corresponding grey scale 129 is shown at the right side of FIG. 7.

The values represented by the grey scale 129 in FIG. 7 range from $2.2 \times 10^4$ to $2.7 \times 10^4$. These values are in arbitrary units and based on light intensities recorded by the detector elements. These values are not directly related to properties of microstructures formed on the wafer. However, it is possible to relate these values to parameter values representing properties of the microstructures formed on the wafer by performing a low number of one or more micro-inspections of locations on the wafer located at positions on the wafer corresponding to windows 111 of the mask 109 used for analyzing the light intensities recorded in the macro-inspection. Micro-inspecting one such location allows to determine at least one parameter value representing a property of the microstructures formed on the wafer at the micro-inspected location, and the value 129 obtained by macro-inspecting the same location can then be translated to this at least one parameter. Other values 129 obtained from macro-inspections of locations not inspected by micro-inspection can also be translated to parameter values representing properties of microstructures formed on the wafer at those other macro-inspected locations by applying a same or similar translation. Such translation may include a calculation based on a function of the parameter values obtained by micro-inspection and values 129 obtained by macro-inspection of corresponding locations. The function can be a linear function having a slope and an offset or some other suitable function, such as a polynomial.

According to an example, one location within each window 111 shown in FIG. 6 is micro-inspected in order to determine at least one parameter representing a property of the wafer at the micro-inspected location, and the values obtained by macro-inspecting the plurality of locations within each window 111 are used to determine at least one parameter representing the property of the wafer at the macro-inspected locations based on the parameter value determined by micro-inspection. Since each window 111 contains plural pixels of the image, it is possible to determine plural parameter values representing properties of the microstructures for each window based on one single macro-inspection and a number of micro-inspections corresponding to the number of windows 111. A low number of micro-inspections allows to generate a large amount of data providing information on the microstructures formed on the wafer, accordingly.

According to other examples, an even lower number of micro-inspections is performed. For example, only one or two or less than some ten micro-inspections are performed at locations within different windows 111. Moreover, it is even possible to perform a low number of micro-inspections such that not even every die or exposure field is covered by one or more micro-inspections. Specifically, according to this example, only locations within windows of a subset of the dies or exposure fields on the wafer are micro-inspected, and the at least one parameter value representing a property of the microstructures of the wafer at the micro-inspected locations is translated to at least one parameter representing properties of the microstructures at all macro-inspected locations.

Parameter values representing properties of the microstructures on the wafer can be obtained for a huge number of macro-inspected locations while only a low number, such as one, five, ten or a few dozen of micro-inspections is performed on the whole wafer.

According to further examples, the at least one parameter value determined for the micro-inspected location comprises at least one value representing at least one thickness of a layer provided on the wafer and at least one value representing an extension of micro-features, in particular lateral extensions of micro-features, provided on the wafer, and wherein the parameter values determined for the macro-inspected locations represent the lateral extensions of the features provided on the wafer, wherein these parameter values are determined based on the light intensities recorded at the macro-inspected locations while taking into account the at least one value representing the at least one thickness determined from the micro-inspected location. For example the layer thickness can be measured at plural locations on the wafer by micro-inspection. Since thicknesses of layers on the wafer typically vary only gradually over the wafer surface, a model representing a distribution of the layer thicknesses across the wafer can be determined from a relatively low number of micro-inspected locations. On the other hand the micro-features are structures rapidly varying in the lateral direction. They have lateral extensions, which can be described by, for example, the critical dimension (CD), a hole diameter or other parameters, and vertical extensions, such as a depth of a hole or trench or other structure. Layers would not be considered as micro-structures as they do not change in the lateral direction and do not have a characteristic lateral dimension.

As mentioned above, layer thicknesses typically vary slowly in the lateral direction on one wafer, and they may vary significantly from wafer to wafer. Moreover, variations of the layer thicknesses change the light intensities recorded in the macro-inspections. The layer thicknesses according the model can than be determined for the macro-inspected locations and used to provide corrections to the parameter values representing the lateral extensions of the features provided on the wafer. Background information relating to determination of layer thicknesses and lateral extensions of features on the wafer can be obtained from the article Karen Dabertrand et. al. "Industrial characterization of scatterometry for advanced APC of 65 nm CMOS logic gate patterning", Proc. Of SPIE Vol. 6922, 69220W (2008), the full content of which is incorporated herein by reference.

Figure 8A:
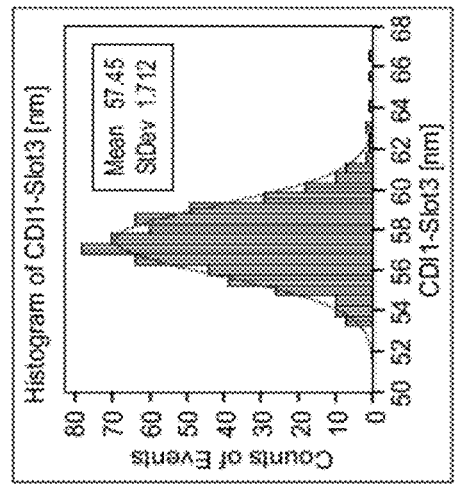
FIGS. 8A-C show images of three different wafers recorded during a manufacturing process.
Figure 8B:
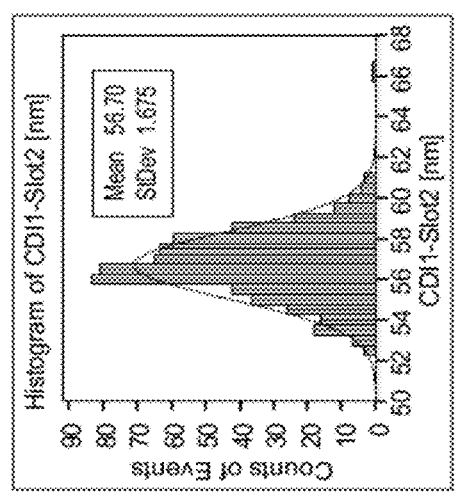
Figure 8C:
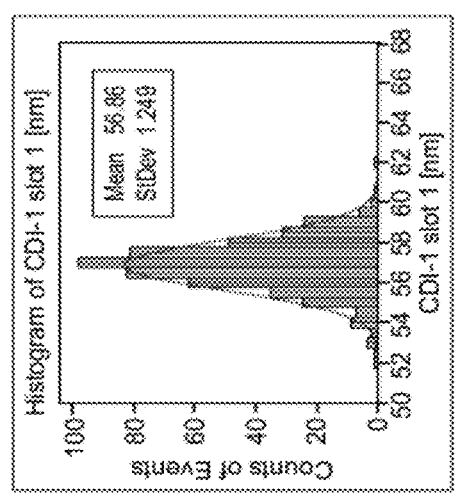

FIGS. 8A, 8B and 8C show images of three different wafers obtained during wafer manufacture by macro-inspection. The images appear to be very similar. A masking operation is applied to the images as illustrated above. This means that only a subset of the recorded image intensities is used for further processing, wherein light intensities recorded by detector elements onto which portion of predefined pattern fields are imaged, are contained in the subset and wherein light intensities recorded by detector elements onto which portions of the pattern fields are not imaged are not contained in the subset. The pattern fields used to determine the subset have a same or similar arrangement pattern of microstructures formed on the wafer. At least one value is determined for each light intensity of the subset. For example, the at least one value can be the detected light intensity itself, or a function of this light intensity. Moreover, this value can be calculated from light intensities detected by a same detector element at different light settings. The light settings may differ with respect to wavelength and/or polarization. A statistical analysis is performed on the values determined for the light intensities of the subset. The statistical analysis is used to determine at least one statistical property of these values. The at least one statistical property may comprise, for example, a mean value, a variance, a skewness and a kurtosis of a distribution of these values, for example.

Figure 9A:
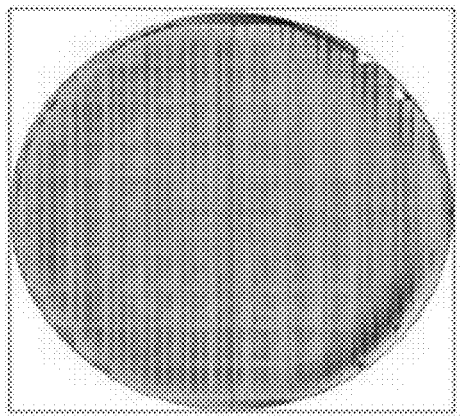
FIGS. 9A-C show charts illustrating statistical properties of values derived from the images shown in FIGS. 8A-C.
Figure 9B:
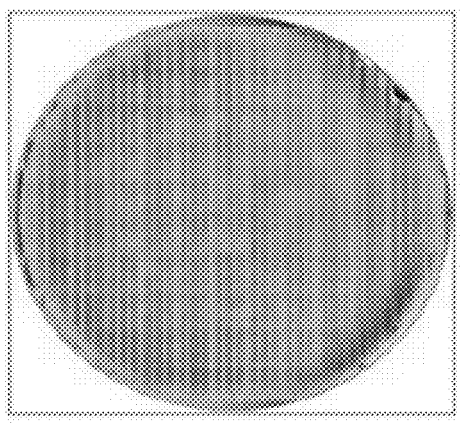
Figure 9C:
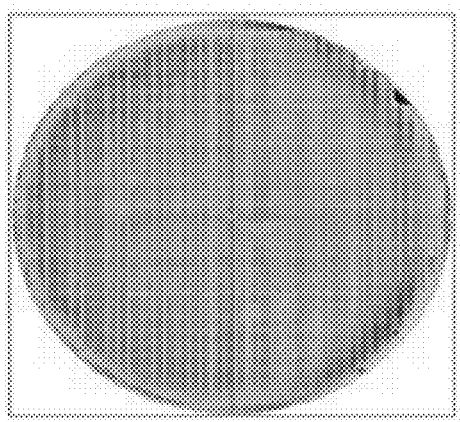

FIGS. 9A, 9B and 9C are charts showing distributions of the values determined from each image shown in FIGS. 8A, 8B and 8C, respectively, and indicating the mean value and variance (standard deviation) as statistical properties of these values.

Even though the images of FIGS. 8A, 8B and 8C appear to be very similar, it is apparent from FIGS. 9A, 9B and 9C that the statistical properties of these images, determined subsequent to a masking process, differ with respect to their mean values and standard deviations. It has been found that changes in statistical properties of the values obtained from images recorded by macro-inspection are indicative for changes of properties of microstructures of wafers manufactured in a manufacturing process of many wafers. Therefore, the at least one statistical property determined from a macro-inspection performed on an individual wafer during a manufacturing process can be compared to predetermined values of the statistical property. For example, threshold values can be set for the determined statistical property, and processing parameters of the wafer manufacturing process can be changed if the statistical property determined from micro-inspection of one or more individual wafers is above or below such threshold value.

Since all dies produced on a wafer are typically intended to be identical, intensity values of all macro-inspected locations on the whole wafer can be included in the processing of the recorded light intensities wherein only those light intensities which correspond to locations on the wafer outside the predefined pattern fields (masked intensities) are not used for determining the at least statistical property.

Figure 10:
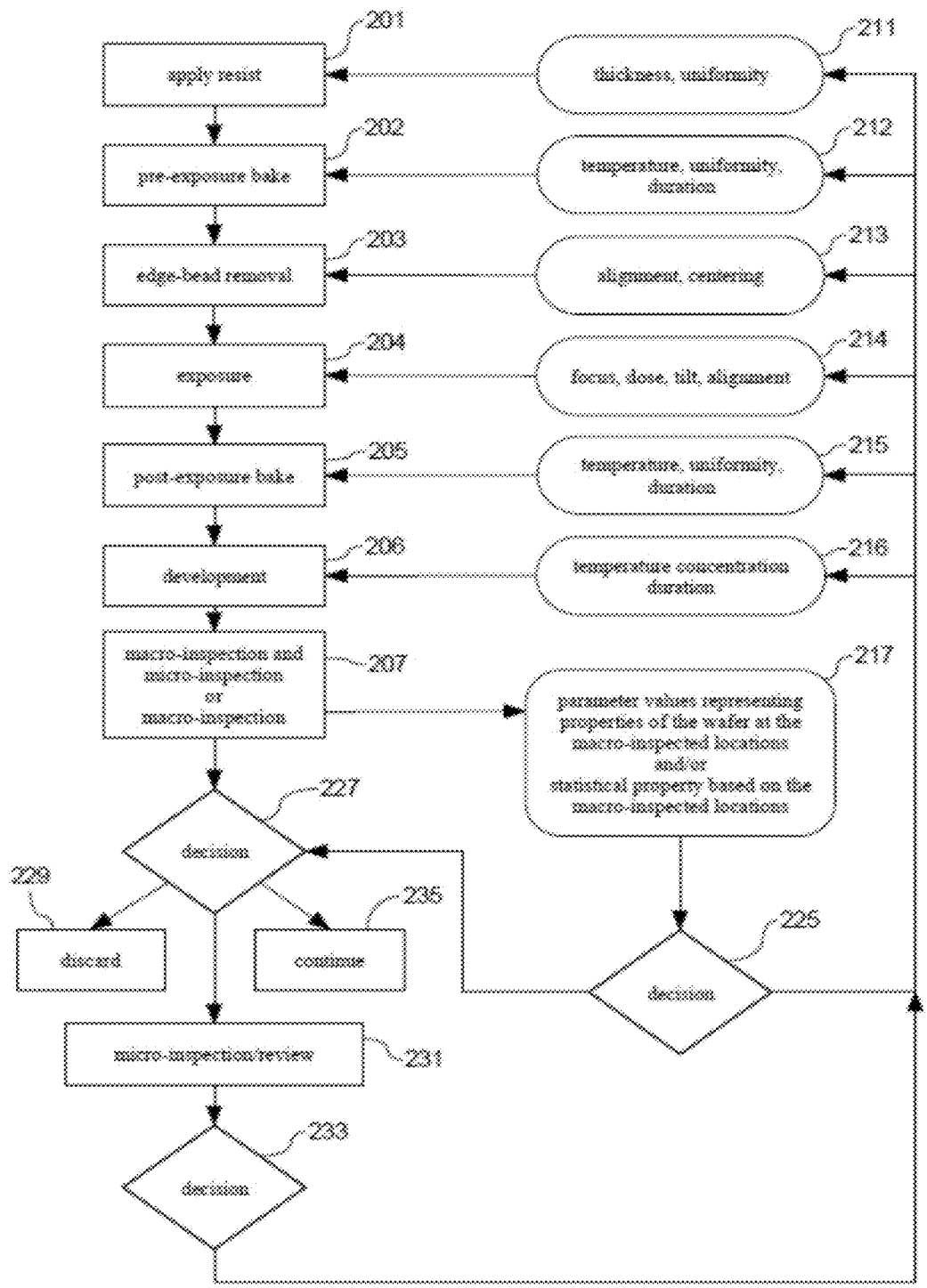
FIG. 10 is a flow chart illustrating a method of manufacturing semiconductor wafers.

FIG. 10 illustrates a method of processing a semiconductor wafer. The method is performed at a litho-cluster which comprises a track system which coats and develops wafers with a resist, linked to a lithography system which images patterns onto a wafer. The method includes plural processing steps 201 to 206 and an inspection step 207. In step 201 a resist layer is applied to the wafer surface, wherein this processing is controlled by process parameters 211, such as a thickness and a uniformity of the applied layer. In a step 202 the wafer undergoes a pre-exposure bake which is controlled by process parameters 212 such as a temperature, a temperature uniformity or a duration of bake. In a subsequent edge bead removal step 203, a portion of the resist layer covering the wafer edge is removed. This processing is controlled by process parameters 213, such as an alignment or centering of the wafer relative to a tool performing the removal of the resist. In a subsequent exposure step 204 the resist is exposed with a pattern, wherein the exposure is controlled by process parameters 214, such as a focus, an exposure dose and a tilt and an alignment of the wafer relative to an exposure tool. Thereafter, a post-exposure bake step 205 is performed, wherein this processing is controlled by process parameters 215, such as a temperature, a temperature uniformity and a duration. In a step 206, the resist is developed, wherein the development is controlled by process parameters 216 such as a temperature, a concentration of applied substances and a duration.

The inspection step 207 comprises a macro-inspection of a huge number of locations on the wafer and a micro-inspection of a relatively low number of locations on the wafer, wherein parameter values representing properties of the wafer at the macro-inspected locations are determined based on light intensities recorded for the macro-inspected locations and on at least one parameter value representing properties of the wafer at the few micro-inspected locations. According to other examples, the inspection 207 comprises only macro-inspection of a huge number of locations on the wafer, wherein at least one statistical property is determined based on light intensities recorded for the macro-inspected locations. The parameter values representing properties of the wafer at the macro-inspected locations and/or the statistical properties are used as an input in a decision step 225. In decision step 225, a determination is made whether the parameter values representing properties of the wafer at the macro-inspected locations are within or outside a desired range and/or whether the statistical properties obtained from the light intensities recorded by macro-inspection of the whole wafer are within or outside desired ranges.

The decision step 225 may include decisions directed to changing the process parameters 211 to 216 based on the determined feature properties. If necessary, the processed parameters are changed to improve the processing in steps 201 to 206 for next wafers undergoing the processing. The analysis performed in decision step 225 may also influence a decision 227 in which a determination is made whether the currently inspected wafer is discarded in a step 229 because the inspection 207 has revealed serious defects and deficiencies of the wafer. If the decision 227 finds that the currently inspected wafer fulfils certain design requirements, the wafer continues to undergo further processing steps 235 of its manufacture.

Since the inspection 207 uses a macro-inspection tool for obtaining information, such as a critical dimension or a line width or other information relating to feature properties of the formed microstructures, the inspection 207 can be performed very rapidly. The result of the inspection can be immediately used to decide on whether the wafer should be further processed or discarded. Further, the information can be used to improve the manufacturing process by changing process parameters controlling processing of following wafers.

In the example illustrated above, the inspection 207 is performed after the development 206. In other examples, the inspection is performed after other processing steps, such as the exposure 204, the pre-exposure bake 202, the application 201 of the resist layer or the post-exposure bake 205. Still further, the inspection can be performed after more than one or all of the processing steps to further improve the control of the individual processing steps.

The decision 227 may also include a decision to perform a micro-inspection and review using an electron microscope, for example, in a step 231.

Based on results of the micro-inspection 231, a decision 233 can be made to change one or more of the process parameters 211 to 216 to improve the processing of other wafers.

Figure 11:
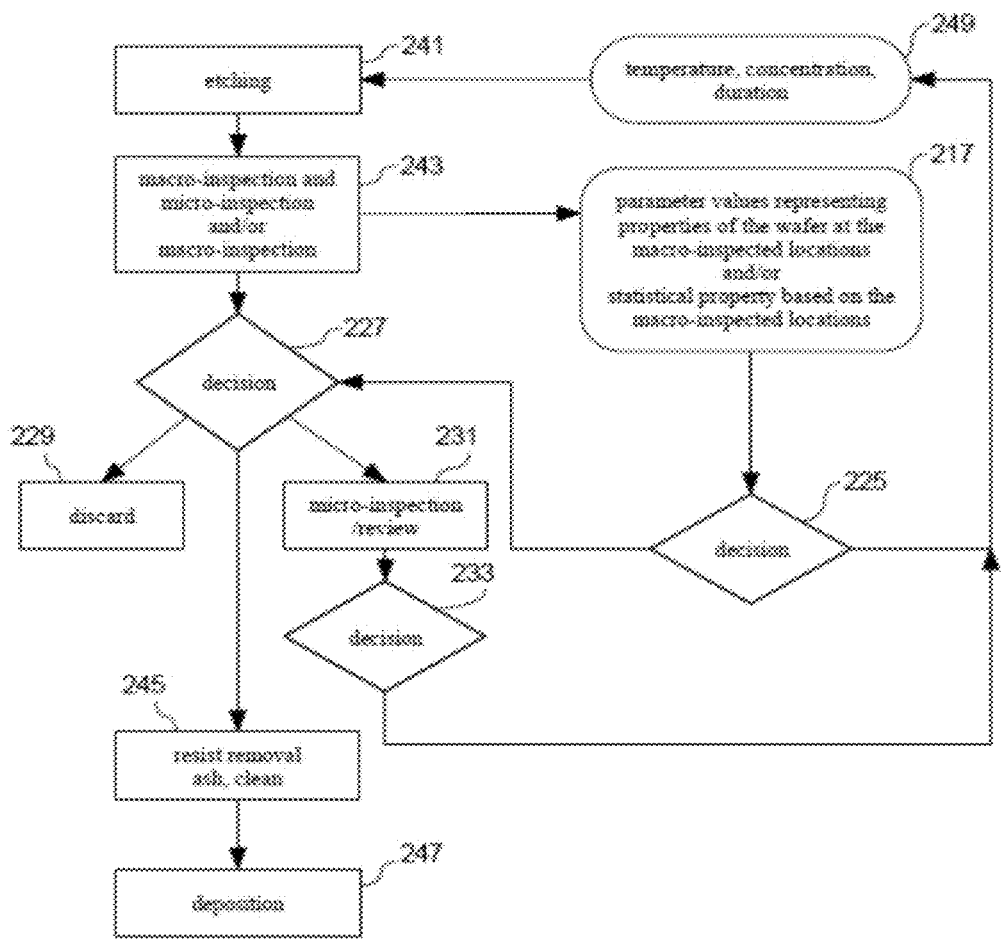
FIG. 11 is a flowchart illustrating a further method of manufacturing of a semiconductor wafers.

FIG. 11 illustrates a further method of processing a semiconductor wafer. This method can be performed subsequent to the method illustrated with reference to FIG. 10 at the continuation step 235. The method illustrated in FIG. 11 can be performed at an etching and deposition process module used in a wafer manufacture. The method includes a processing step 241 in which the pattern of the developed resist is transferred to the wafer substrate by etching. The etching is controlled by process parameters 249, such as a temperature, a concentration and a duration of the processing.

After the etching 241, an inspection 243 is performed. Again, this inspection may comprise a combination of macro-inspection and micro-inspection in order to determine parameter values representing properties of the wafer at the macro-inspected locations, or a macro-inspection, which is not necessarily accompanied by a micro-inspection, in order to determine statistical properties of the wafer based on macro-inspection, as illustrated above with reference to FIG. 10.

Also decision steps 225 and 227 as already illustrated above are performed to discard 229 the wafer, perform a micro-inspection/review 231 as illustrated above and to perform a decision step 233 based thereon, or to continue with the manufacture of the wafer at a step 245, in which the developed resist remaining on the wafer is removed in an ash process and a cleaning process.

The decision in step 225 may also include changing the process parameters 249 determining the etching process 241 to improve manufacture of subsequent wafers. Similarly, the decision in step 225 may also include changing the process parameters 211 to 217 (see FIG. 10) determining the processing steps 201 to 206 as illustrated with reference to FIG. 10 to improve manufacture of subsequent wafers.

Figure 12:
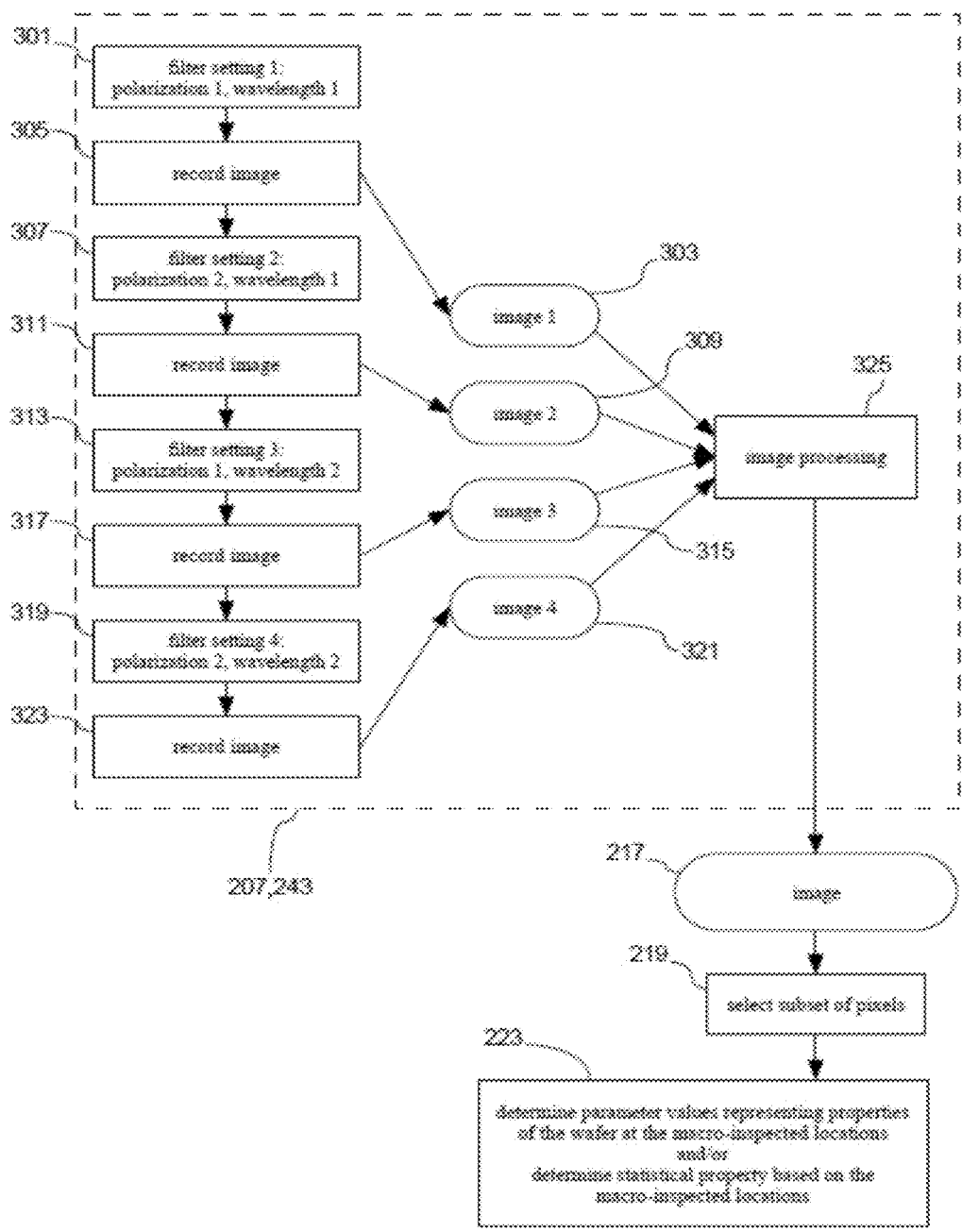
FIG. 12 is a flowchart illustrating a detail of an inspection which can be used in one of the methods illustrated in FIGS. 10 and 11.

FIG. 12 is a flowchart illustrating a detail of an embodiment of the inspection which can be used, for example, in step 207 of the method illustrated with reference to FIG. 11 or step 243 of the method illustrated with reference to FIG. 12.

In the method shown in FIG. 12, a macro-inspection comprises recording of more than one image of a same wafer maintained at a same position relative to the inspection system used. The plural recorded images differ with respect to a setting of the light used for illuminating the wafer and/or the light used for imaging the wafer. The different settings of the light may include settings with respect to a spectral distribution of the light and a polarization of the light. The settings can be selected with suitable optical filters.

In a step 301, a first light setting is selected by controlling the filters such that light of a first wavelength range from, for example, 410 nm to 450 nm and central wavelength of 430 nm polarized according to a first polarization direction can be used to record an image. A first image 303 is recorded using this setting in a step 305.

In a subsequent step 307, a second light setting is selected by controlling the filters such that light of a the first wavelength range polarized according to a second polarization direction orthogonal to the first polarization direction can be used to record an image. A second image 309 is recorded using this setting in a step 311.

In a subsequent step 313, a third light setting is selected by controlling the filters such that light of a second wavelength range from, for example, 630 nm to 670 nm and central wavelength of 650 nm polarized according to the first polarization direction can be used to record an image. A third image 315 is recorded using this setting in a step 317.

In a subsequent step 319, a fourth light setting is selected by controlling the filters, such that light of a the second wavelength range polarized according to the second polarization direction can be used to record an image. A fourth image 321 is recorded using this setting in a step 323.

The four recorded images 303, 309, 315, 321 undergo an image processing in a step 325 to calculate a new image 217. The new image 217 is calculated pixel by pixel, wherein pixel intensities of each pixel are calculated based on pixel intensities of corresponding pixels of each of the images 303, 309, 315, 321.

For example, the pixel intensity of pixels of the new image can be calculated according to the formula $$I_n = \frac{a_1 I_1}{a_2 I_2} - \frac{a_3 I_3}{a_4 I_4},$$

wherein $I_n$ is the pixel intensity of the pixel in the new image 217, $I_1$ is the pixel intensity of the pixel in the first image 303, $I_2$ is the pixel intensity of the pixel in the second image 309, $I_3$ is the pixel intensity of the pixel in the third image 315, $I_4$ is the pixel intensity of the pixel in the fourth image 321, and $a_1$, $a_2$, $a_3$ and $a_4$ are suitably chosen constants.

The image 217 calculated from the four images 303, 309, 315 and 321 is then processed as already illustrated above, i.e. a masking operation is applied in a step 219, such that a subsequent processing is based on only a subset of the image pixels, and in a subsequent step 223, at least one statistical property is determined based on the light intensities corresponding to the macro-inspected locations.

While certain exemplary embodiments are disclosed herein, alternatives, modifications and variations will be apparent to those skilled in the art. Accordingly, the exemplary embodiments set forth herein are intended to be illustrative and not limiting in any way. Various changes may be made without departing from the spirit and scope of the present disclosure.

What is claimed is:

1. A method of manufacturing a plurality of semiconductor wafers, wherein each wafer has plural dies, wherein the plural dies include corresponding pattern fields in which microstructures are arranged according to a same arrangement pattern, and wherein the method comprises:

micro-inspecting at least one location within at least one micro-inspected pattern field and determining at least one parameter value representing a property of the wafer at the micro-inspected location, wherein the micro-inspecting comprises directing measuring radiation to the location and detecting radiation emerging from the location using magnifying optics;

macro-inspecting a plurality of locations within the at least one micro-inspected pattern field, wherein the macro-inspecting comprises directing measuring light to plural pattern fields, imaging the illuminated plural pattern fields onto an array of detector elements using demagnifying optics and recording light intensities detected by the detector elements, wherein each of the locations is simultaneously imaged onto one or more adjacent detector elements, and wherein a number of the macro-inspected locations within each of the at least one micro-inspected pattern fields is at least 5 times greater than a number of the micro-inspected locations within this pattern field; and determining, for each macro-inspected location of the macro-inspected pattern field, at least one parameter value representing the property of the wafer at the macro-inspected location based on the light intensity recorded for the macro-inspected location and on the at least one parameter value representing the property of the wafer at the micro-inspected location of this pattern field.

2. The method according to claim 1, further comprising:
macro-inspecting a plurality of locations within at least one additional pattern field which does not contain a micro-inspected location, and determining, for each macro-inspected location of the additional pattern field, at least one parameter value representing the property of the wafer at the macro-inspected location based on the light intensity recorded for the macro-inspected location and on the parameter value representing the property of the wafer at at least one micro-inspected location.

3. The method according to claim 2, wherein the parameter value representing the property of the wafer at the at least one micro-inspected location and forming a basis for the determining of the at least one parameter value representing the property of the wafer at the macro-inspected location includes the parameter value representing the property of the wafer at that micro-inspected location among plural micro-inspected locations which is closest to the respective macro-inspected location.

4. The method according to claim 1, wherein the macro-inspecting comprises directing measuring radiation simultaneously to plural dies and imaging the illuminated plural dies onto the array of detector elements.

5. The method according to claim 4, wherein the macro-inspecting comprises directing measuring radiation simultaneously to the whole wafer and imaging the whole wafer onto the array of detector elements.

6. The method according to claim 4, wherein the macro-inspecting further includes spatial frequency filtering of the recorded light intensities, and wherein the determining, for each macro-inspected location of the macro-inspected pattern field, of the at least one parameter value representing the property of the wafer at the macro-inspected location is based on the spatial frequency filtered light intensity recorded for the macro-inspected location and on the at least one parameter value representing the property of the wafer at the micro-inspected location of this pattern field, and wherein the spatial frequency filtering comprises at least one of high-pass filtering and low-pass filtering.

7. The method according to claim 1, wherein a region on the wafer to which measuring radiation is directed in the micro-inspecting has a first surface area, and wherein each of the locations imaged onto the one or more detector elements in the macro-inspecting has a second surface area which is at least 2 times greater than the first surface area.

8. The method according to claim 1, wherein the measuring radiation of the micro-inspecting comprises measuring light focused onto the wafer, and wherein the radiation emerging from the location comprises measuring light having interacted with the wafer.

9. The method according to claim 8, wherein the micro-inspecting comprises recording intensities of detected radiation in dependence of a wavelength of detected light.

10. The method according to claim 8, wherein the micro-inspecting comprises recording intensities of detected radiation in dependence of a polarization of detected light.

11. The method according to claim 8, wherein the micro-inspecting is performed using a spectrometer.

12. The method according to claim 8, wherein the at least one parameter value determined for the micro-inspected location comprises at least one value representing at least one thickness of a layer provided on the wafer and at least one value representing an extension of micro-features provided on the wafer, and wherein the parameter values determined for the macro-inspected locations represent the lateral extensions of features provided on the wafer, wherein these parameter values are determined based on the light intensities recorded at the macro-inspected locations while taking into account the at least one value representing the at least one thickness determined from the micro-inspected location.

13. The method according to claim 12, wherein the micro-inspecting is performed using a scanning electron microscope.

14. The method according to claim 1, wherein the measuring radiation of the micro-inspecting comprises a charged particle beam focused onto the wafer, and wherein the radiation emerging from the location comprises charged particles.

15. The method according to claim 14, wherein the charged particle beam is scanned across the location.

16. The method according to claim 1, comprising sequentially micro-inspecting plural locations within plural different micro-inspected pattern fields.

17. The method according to claim 1, wherein the macro-inspecting comprises providing at least two different light settings and recording light intensities detected by the detector elements for each of the at least two different light settings.

18. The method according to claim 17, wherein the at least two different light settings differ with respect to at least one of wavelength and polarization.

19. The method according to claim 17, wherein the light recorded by the detector elements in a first light setting has a first spectral distribution, wherein the light recorded by the detector elements in a second light setting has a second spectral distribution, and wherein a central wavelength of the first spectral distribution differs from a central wavelength of the second spectral distribution by more than 30 nm.

20. The method according to claim 19, wherein a width of each of the first and second spectral distributions is smaller than 100 nm.

21. The method according to claim 17, wherein the light recorded by the detector elements in a first light setting has a first polarization direction, wherein the light recorded by the detector elements in a second light setting has a second polarization direction, and wherein the first polarization direction differs from the second polarization direction by more than 10°.

22. The method according to claim 1, wherein the at least one parameter value represents a line width, a feature side wall angle, a feature height, a corner rounding of a feature, a critical dimension (CD), an overlay shift and a layer thickness of the microstructures arranged in the pattern field.

23. The method according to claim 1, further comprising processing the wafers using at least one processing parameter; and
changing the at least one processing parameter based on the parameter values determined for the macro-inspected locations.

24. A method of manufacturing a plurality of semiconductor wafers, wherein each wafer has plural dies, wherein the plural dies include corresponding pattern fields in which microstructures are arranged according to a same arrangement pattern, and wherein the method comprises:
processing the wafers using at least one processing parameter;
macro-inspecting a plurality of locations within at least one pattern field in each of plural dies of a wafer, wherein the macro-inspecting comprises directing measuring light to the pattern fields, imaging the illuminated plural pattern fields onto an array of detector elements and recording light intensities detected by the detector elements, wherein each of the locations is simultaneously imaged onto one or more adjacent detector elements; and
processing the recorded light intensities by:
selecting a subset of the recorded light intensities, wherein light intensities recorded by detector elements onto which portions of the pattern fields are imaged are contained in the subset and wherein light intensities recorded by detector elements onto which portions of the pattern fields are not imaged are not contained in the subset,
determining, for each light intensity of the subset, at least one value based on the light intensity, and
determining at least one statistical property of the values for each wafer; and
wherein the method further comprises changing the at least one processing parameter based on a comparison of the determined statistical property with predetermined values of the statistical property.

25. The method according to claim 24, wherein the at least one statistical property comprises a moment of a distribution of the values for each wafer.

26. The method according to claim 24, wherein the at least one statistical property comprises at least one of a variance, a skewness and a kurtosis of a distribution of the values for each wafer.

27. The method according to claim 24, wherein the macro-inspecting comprises directing measuring radiation simultaneously to plural dies and imaging the illuminated plural dies onto the array of detector elements.

28. The method according to claim 24, wherein the macro-inspecting comprises directing measuring radiation simultaneously to the whole wafer and imaging the whole wafer onto the array of detector elements.

29. The method according to claim 24, wherein the macro-inspecting comprises providing at least two different light settings and recording light intensities detected by the detector elements for each of the at least two different light settings;
wherein the selecting of the subset of light intensities comprises selecting the subset of light intensities recorded for each of the light settings;
wherein the determining of the at least one value based on the light intensity comprises determining the at least one value based on corresponding light intensities recorded for each of the light settings.

30. The method according to claim 24, wherein the changing of the at least one processing parameter is based on the comparison of the determined statistical property with the predetermined values of the statistical property and without involving any micro-inspection of locations of the wafer having a diameter smaller than an extension of a portion of the wafer imaged onto one single detector element of the array of detector elements used in the macro-inspecting.

31. The method according to claim 24, wherein the processing comprises exposing the wafer with a pattern, wherein the at least one processing parameter comprises in particular an exposure dose and a focus used in the exposing; and/or
wherein the processing comprises etching, wherein the at least one processing parameter comprises in particular an etch time, a etch temperature, and a concentration of a medium used in the etching; and/or
wherein the processing comprises a deposition of material on the wafer, wherein the at least one processing parameter comprises in particular a concentration, a temperature and a duration.

32. The method according to claim 24, wherein the processing comprises:
coating the wafer with a resist;
exposing a pattern onto the resist after the coating;
developing the patterned resist after the exposing;
etching the wafer through the patterned resist after the developing; and
removing the resist remaining on the wafer after the etching; and
wherein the macro-inspecting is performed after the etching of the wafer and before the removing of the remaining resist.

* * * * *